United States Patent
Yangdai et al.

(10) Patent No.: US 11,612,308 B2
(45) Date of Patent: Mar. 28, 2023

(54) CONTROL METHOD, CONTROL SYSTEM, ELECTRONIC DEVICE AND READABLE STORAGE MEDIUM FOR CAPSULE ENDOSCOPE

(71) Applicant: ANKON TECHNOLOGIES CO., LTD, Wuhan (CN)

(72) Inventors: Tianyi Yangdai, Wuhan (CN); Hao Liu, Wuhan (CN); Xinhong Wang, San Diego, CA (US)

(73) Assignee: ANKON TECHNOLOGIES CO., LTD, Wuhan (CN)

( * ) Notice: Subject to any disclaimer, the term of this patent is extended or adjusted under 35 U.S.C. 154(b) by 283 days.

(21) Appl. No.: 17/019,032

(22) Filed: Sep. 11, 2020

(65) Prior Publication Data
US 2021/0068638 A1    Mar. 11, 2021

(30) Foreign Application Priority Data
Sep. 11, 2019 (CN) .......................... 201910856996.9

(51) Int. Cl.
  *A61B 1/04* (2006.01)
  *A61B 1/00* (2006.01)
(52) U.S. Cl.
  CPC .......... *A61B 1/041* (2013.01); *A61B 1/00006* (2013.01); *A61B 1/00158* (2013.01)
(58) Field of Classification Search
  CPC .......... A61B 1/00158; A61B 2034/731; A61B 34/73; A61B 5/073
  See application file for complete search history.

(56) References Cited

U.S. PATENT DOCUMENTS

2007/0221233 A1* 9/2007 Kawano ................. A61B 5/062
  128/899
2007/0265496 A1* 11/2007 Kawano ............. A61B 1/00158
  600/109

(Continued)

FOREIGN PATENT DOCUMENTS

| CN | 105559739 A | 5/2016 |
| CN | 106963324 A | 7/2017 |
| CN | 107773205 A | 3/2018 |

*Primary Examiner* — John P Leubecker
*Assistant Examiner* — Jae Woo
(74) *Attorney, Agent, or Firm* — Treasure IP Group, LLC

(57) ABSTRACT

A control method, a control system, an electronic device and a readable storage medium for a capsule endoscope are disclosed. The method comprises: obtaining the initial distance H between the capsule endoscope and an external magnetic field generating device based on magnetic field information when the capsule endoscope is positioned in the vertical direction of the magnetic field generating device in an initial state; presetting a target area according to the force balance of the in vivo capsule endoscope, and adjusting the distance between a second permanent magnet and the capsule endoscope to locate the capsule endoscope in the target area; monitoring the acceleration of the capsule endoscope, and determining the vertical component of acceleration of the capsule endoscope; and adjusting the current of the electromagnetic induction coil according to the vertical component of the acceleration to finely adjust the force balance of the capsule endoscope in the target area.

10 Claims, 4 Drawing Sheets

(56) References Cited

U.S. PATENT DOCUMENTS

| | | | | |
|---|---|---|---|---|
| 2007/0270628 A1* | 11/2007 | Kawano | ................. | A61B 34/73 |
| | | | | 600/12 |
| 2012/0095289 A1* | 4/2012 | Kawano | ............. | A61B 1/00158 |
| | | | | 600/109 |
| 2012/0095290 A1* | 4/2012 | Kawano | ............. | A61B 1/00158 |
| | | | | 600/117 |
| 2015/0297869 A1* | 10/2015 | Mesallum | .............. | A61B 34/10 |
| | | | | 604/528 |
| 2017/0156574 A1* | 6/2017 | Kawano | ................... | A61B 1/00 |

* cited by examiner

CONTROL METHOD, CONTROL SYSTEM, ELECTRONIC DEVICE AND READABLE STORAGE MEDIUM FOR CAPSULE ENDOSCOPE

CROSS-REFERENCE OF RELATED APPLICATIONS

The application claims priority to Chinese Patent Application No. 201910856996.9 filed on Sep. 11, 2019, the contents of which are incorporated by reference herein.

FIELD OF INVENTION

The present invention relates to a medical device, and more particularly to a control method, a control system, an electronic device and a readable storage medium for a capsule endoscope.

BACKGROUND

Capsule endoscope is a medical device. It integrates the core components such as a camera and a wireless transmission antenna into a capsule that can be swallowed by a subject. During an examination, the capsule endoscope is swallowed into the body of the subject, and then takes images in the digestive tract while transmitting the images to the outside of the body for review and evaluation by a physician.

In order to improve the control flexibility of the capsule endoscope during gastrointestinal examination to improve positioning accuracy, the capsule endoscope is required to have the ability to actively control its motion. The power for the active control comes mainly from the propulsion device such as a motor inside the capsule, or from an external magnetic field. To reduce the size and working power of the capsule, the most dominant active control method is to control by an external magnetic field. The principle of the method is: the capsule endoscope has a small inbuilt permanent magnet, and an external controller controls the orientation of the capsule endoscope in human body with a large permanent magnet.

However, the current external active control method is mainly an open-loop control, which lacks accurate feedback of the actual physical space position or motion state of the capsule. Therefore, the control accuracy of the capsule endoscope is limited. For example, in the prior art, usually, the capsule endoscope in the digestive tract can only be in three positions: bottom, top, or liquid level. If the capsule endoscope can be stably suspended in the stomach cavity, while also being free to move and adjust, the accuracy of control can be greatly improved.

In the prior art, in order to suspend the capsule endoscope in the target area, the following method is usually used for control. The Patent Publication No. CN 107773205A, which named "Magnetic Control System for Capsule Endoscope" discloses that: an external magnetic field generation module comprises a permanent magnet that generates a basic magnetic field and an electromagnetic coil that generates a variable magnetic field; and a Hall sensor is provided in the capsule endoscope to sense the strength of the external magnetic field, thereby estimating the position of the capsule endoscope in the vertical direction. While this method provides a closed-loop feedback on the position of the capsule endoscope, it does have the following problems in practice. Problem 1: low signal-to-noise ratio. In the embodiment of the referenced invention, the Hall sensor needs to be arranged inside the capsule endoscope. Since the Hall sensor is close to the magnet inside the capsule, the magnetic field strength of the magnet at a magnetic sensor is about 10 mT. Moreover, in the vicinity of the stabilized magnetic levitation point, to overcome the gravity of the capsule endoscope, the basic magnetic field strength of the external magnetic field generation module is usually 1~10 mT. Therefore, the Hall sensor needs to sense the slight jitter of the capsule endoscope at a reference magnetic field strength level of 10~10² mT. In a complex electromagnetic environment, the magnetic field generated by the surrounding equipment is strong, such as 0.01~0.1 mT, and there are also fluctuations with time and position. As a result, the method of position feedback by measuring magnetic field strength comes with a problem of low signal-to-noise ratio which affects control accuracy. Problem 2: High power consumption. The Hall sensor usually has a high power consumption. Taking the MLX90393 sensor as an example, the operating voltage is 1V and the nominal operating current is 100 μA. Therefore, it is not conducive to a long-term suspension of the capsule endoscope designed with this method.

SUMMARY OF THE INVENTION

To solve the problems, the present invention aims to provide a control method, a control system, an electronic device and a readable storage medium for a capsule endoscope.

To achieve one of the above-mentioned objects of the invention, an embodiment of the present invention provides a control method for a capsule endoscope, the method comprising: step S1, providing an external magnetic field generating device and an in vivo capsule endoscope, wherein the capsule endoscope is positioned in the vertical direction of the magnetic field generating device in an initial state, and obtaining the initial distance H between the capsule endoscope and the external magnetic field generating device based on magnetic field information in the initial state; wherein, the capsule endoscope comprises a first permanent magnet, a magnetic sensor and an acceleration sensor; and the external magnetic field generating device comprises a second permanent magnet for generating a strong basic magnetic field and an electromagnetic induction coil for generating a strength-adjustable auxiliary magnetic field by applying a variable current;

step S2, presetting a target area according to the force balance of the in vivo capsule endoscope, wherein the distance between the second permanent magnet and the target area is H1, and adjusting the distance between the second permanent magnet and the capsule endoscope to locate the capsule endoscope in the target area;

step S3, monitoring the acceleration of the capsule endoscope through the acceleration sensor after determining that the capsule endoscope is in the target area, and determining the vertical component of acceleration of the capsule endoscope; and adjusting the current of the electromagnetic induction coil according to the vertical component of the acceleration to finely adjust the force balance of the capsule endoscope in the target area.

In an embodiment, the step S1 specifically comprises: step S11, obtaining magnetic field strength $\vec{B}_{mag}$ detected by the magnetic sensor in the initial state, and calculating magnetic field strength $\vec{B}_E$ generated by the second permanent magnet at the capsule endoscope according to the magnetic field strength $\vec{B}_{mag}$;

$\vec{B}_E = \vec{B}_{mag} - \vec{B}_{in} - \vec{B}_{bg}$, wherein, $\vec{B}_{in}$ is magnetic field strength of the first permanent magnet at the magnetic sensor, and $\vec{B}_{bg}$ is the environmental background magnetic field strength;

step S12, calculating the distance difference H between the capsule endoscope and the second permanent magnet according to the calculated $\vec{B}_E$.

In an embodiment, the step S2 specifically comprises:

step S21, calculating the distance H1 between the second permanent magnet and the target area according to the pulling force $\vec{F}_{pm}$ of the second permanent magnet on the capsule endoscope, wherein the force of the capsule endoscope in the target area is as follows: $\vec{G} + \vec{F}_{pm} + \vec{F}_b \approx 0$, wherein, $\vec{G}$ is the gravity of the capsule endoscope, $\vec{F}_{pm}$ is the pulling force of the second permanent magnet on the capsule endoscope, $\vec{F}_b$ is the buoyant force of the capsule endoscope completely immersed in the liquid, $\vec{G}$ and $\vec{F}_b$ are all given values;

step S22, moving the second permanent magnet in the vertical direction, by a distance of H–H1, to locate the capsule endoscope in the target area.

In an embodiment, the step S3 specifically comprises: monitoring whether the absolute value of the vertical component of acceleration of the capsule endoscope is less than a certain threshold; controlling the electromagnetic induction coil to turn off when the absolute value is less than the certain threshold;

controlling the electromagnetic induction coil to turn on when the absolute value is not less than the certain threshold, adjusting the input current I of the electromagnetic induction coil to adjust the strength of the auxiliary magnetic field, and thereby adjusting the pushing force or pulling force on the capsule endoscope, so that the absolute value of the vertical component of acceleration of the capsule endoscope is less than the certain threshold;

wherein, I=U(t)/R, $$U(t) = K_P\left[e(t) + \frac{1}{T_i}\int e(t)dt + T_d \frac{de(t)}{dt}\right],$$

e(t)=0−$a_z$(t), t denotes time, U(t) is the voltage across the electromagnetic induction coil, R is the resistance of the electromagnetic induction coil, $K_p$ is the proportionality coefficient, $T_i$ is the integral time constant, $T_d$ is the derivative time constant, $a_z$(t) is the vertical component of acceleration of the capsule endoscope at time t, ∫e(t)dt is integral operation, $$\frac{de(t)}{dt}$$

is derivative operation.

In an embodiment, the method further comprises: adjusting the second permanent magnet to move toward and/or away from the capsule endoscope in the vertical direction when the absolute value of the vertical component of acceleration of the capsule endoscope is less than the certain threshold, and determining whether the new height difference between the capsule endoscope and the second permanent magnet is within an effective range; keeping monitoring the new height difference when the new height difference is within the effective range;

adjusting the distance difference between the second permanent magnet and the capsule endoscope, and performing the step S1 cyclically when the new height difference is not within the effective range.

In order to solve one of the objects, an embodiment of the present invention provides an electronic device, comprising a memory and a processor, the memory stores a computer program that can run on the processor, and the processor executes the program to implement the steps of the control method for the capsule endoscope described above.

In order to solve one of the objects, an embodiment of the present invention provides a computer-readable storage medium, storing computer programs, the computer programs can be executed by the processor to implement the steps of the control method for the capsule endoscope described above.

In order to solve another of objects, an embodiment of the present invention provides a control system for the capsule endoscope, the system comprises: a capsule endoscope, comprising a first permanent magnet, a magnetic sensor and an acceleration sensor;

an external magnetic field generating device, which is positioned in the vertical direction of the capsule endoscope in an initial state, comprising: a second permanent magnet for generating a strong basic magnetic field and an electromagnetic induction coil for generating a strength-adjustable auxiliary magnetic field by applying a variable current;

a coarse adjustment module, used for presetting a target area according to the force balance of the in vivo capsule endoscope, and the distance between the second permanent magnet and the target area is H1;

the coarse adjustment module is also used for obtaining an initial distance H between the capsule endoscope and the external magnetic field generating device in the initial state according to the magnetic field information, and adjusting the distance between the second permanent magnet and the capsule endoscope according to the magnitude relationship between H and H1, so as to locate the capsule endoscope in the target area;

a fine adjustment module, used for monitoring the acceleration of the capsule endoscope through the acceleration sensor after determining that the capsule endoscope is in the target area, determining the vertical component of acceleration of the capsule endoscope, and adjusting the current of the electromagnetic induction coil according to the vertical component of the acceleration to finely adjust the force balance of the capsule endoscope in the target area.

In an embodiment, the coarse adjustment is specifically used for: obtaining magnetic field strength $\vec{B}_{mag}$ detected by the magnetic sensor in the initial state, and calculate magnetic field strength $\vec{B}_E$ generated by the second permanent magnet at the capsule endoscope according to the magnetic field strength $\vec{B}_{mag}$;

then, $\vec{B}_E = \vec{B}_{mag} - \vec{B}_{in} - \vec{B}_{bg}$, wherein, $\vec{B}_{in}$ is magnetic field strength of the first permanent magnet at the magnetic sensor, and $\vec{B}_{bg}$ is the environmental background magnetic field strength;

calculating the distance difference H between the capsule endoscope and the second permanent magnet according to the calculated $\vec{B}_E$.

In an embodiment, the coarse adjustment module is specifically used for: calculating the distance H1 between the second permanent magnet and the target area according to the pulling force of the second permanent magnet on the capsule endoscope, wherein the force of the capsule endoscope in the target area is as follows: $\vec{G}+\vec{F}_{pm}+\vec{F}_b \approx 0$, wherein, $\vec{G}$ is the gravity of the capsule endoscope, $\vec{F}_{pm}$ is the pulling force of the second permanent magnet on the capsule endoscope, $\vec{F}_b$ is the buoyant force of the capsule endoscope completely immersed in the liquid, $\vec{G}$ and $\vec{F}_b$ are all given values;

moving the second permanent magnet in the vertical direction, by a distance of H–H1, to locate the capsule endoscope in the target area.

In an embodiment, the fine adjustment module is specifically used for: monitoring whether the absolute value of the vertical component of acceleration of the capsule endoscope is less than a certain threshold; controlling the electromagnetic induction coil to turn off when the absolute value is less than the certain threshold;

controlling the electromagnetic induction coil to turn on when the absolute value is not less than the certain threshold, adjusting the input current I of the electromagnetic induction coil to adjust the strength of the auxiliary magnetic field, and thereby adjusting the pushing force or pulling force on the capsule endoscope, so that the absolute value of the vertical component of acceleration of the capsule endoscope is less than the certain threshold;

wherein, I=U (t)/R, $$U(t) = K_p \left[ e(t) + \frac{1}{T_i} \int e(t)dt + T_d \frac{de(t)}{dt} \right],$$

e(t)=0–a$_z$(t), t denotes time, U(t) is the voltage across the electromagnetic induction coil, R is the resistance of the electromagnetic induction coil, $K_p$ is the proportionality coefficient, $T_i$ is the integral time constant, $T_d$ is the derivative time constant, a$_z$(t) is the vertical component of acceleration of the capsule endoscope at time t, ∫e(t)dt is integral operation, $$\frac{de(t)}{dt}$$

is derivative operation.

In an embodiment, the system further comprises: a feedback module, used for adjusting the second permanent magnet to move toward and/or away from the capsule endoscope in the vertical direction when the absolute value of the vertical component of acceleration of the capsule endoscope is less than the certain threshold, and determining whether the new height difference between the capsule endoscope and the second permanent magnet is within an effective range; keeping monitoring the new height difference when the new height difference is within the effective range;

adjusting the distance difference between the second permanent magnet and the capsule endoscope, and making the absolute value of the vertical component of acceleration of the capsule endoscope less than the threshold when the new height difference is not within the effective range.

Compared with the prior art, the beneficial effect of the present invention is that: the control method, control system, electronic device and readable storage medium of the present invention, the acceleration value measured by the acceleration sensor arranged in the capsule is directly used as the feedback signal during the suspension control, and achieves the objective of capsule suspension by a closed-loop control.

DETAILED DESCRIPTION

The present invention can be described in detail below with reference to the accompanying drawings and preferred embodiments. However, the embodiments are not intended to limit the invention, and the structural, method, or functional changes made by those skilled in the art in accordance with the embodiments are included in the protection scope of the present invention.

The capsule endoscope 100 refers to a capsule-shaped device that can be swallowed into a human body, and is usually located in the intestinal tract of the human body during an examination to take images of the intestinal tract for external processing.

Figure 1:
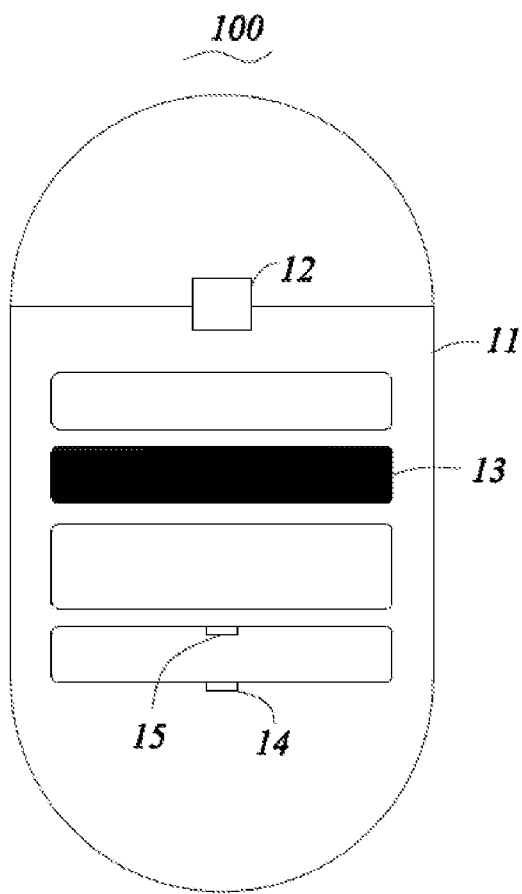
FIG. 1 is a schematic diagram of a capsule endoscope in an embodiment of the present invention.

Referring to FIG. 1, in a specific embodiment of the present invention, the capsule endoscope 100 comprises: a biocompatible enclosure 11, an image acquisition unit 12 arranged inside the enclosure 11, a first permanent magnet 13, a magnetic sensor 14, and an acceleration sensor 15. In addition to these components, the capsule endoscope 100 further comprises modules such as an electrical control circuit and an communication circuit.

Preferably, the image acquisition unit 12 is usually a camera, which is used to observe the environment in the digestive tract and capture and output images. The front end of the enclosure 11 corresponding to the image acquisition unit 12 is an optical front enclosure to provide a better imaging environment. The magnetic sensor 14 is arranged with a distance, that is usually ≥10 mm, from the first permanent magnet 13, in order to roughly estimate the distance between the capsule endoscope 100 and an external magnetic field generating device 200 and assist the magnetic control for suspension of the capsule endoscope 100. The acceleration sensor 15 is used to detect the motion state of the capsule endoscope 100 in the human body. In particular, in this system, an acceleration parameter measured by the acceleration sensor 15 is used as a feedback parameter of the motion state of the capsule endoscope 100 for proportionalintegral-derivative (PID) control of magnetic suspension. The description can continue in the following.

Figure 2:
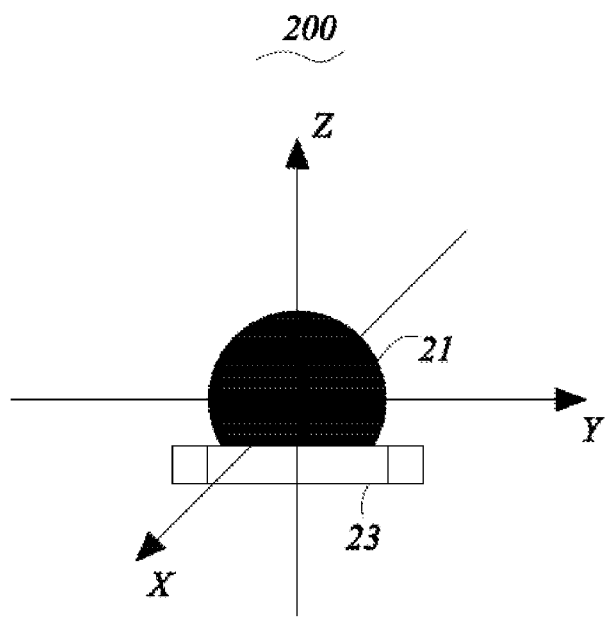
FIG. 2 is a schematic diagram of an external magnetic field generating device in an embodiment of the present invention.

Normally, the capsule endoscope 100 works in conjunction with the external magnetic field generating device 200. The external magnetic field generating device 200 comprises a second permanent magnet configured to generate a strong basic magnetic field, and an electromagnetic induction coil configured to generate a strength-adjustable auxiliary magnetic field by applying a variable current. Referring to FIG. 2, in a specific embodiment of the present invention, the second permanent magnet 21 is spherical or cylindrical in shape. For example, the second permanent magnet 21 is composed of NdFeB N55 magnet with a diameter of about 200 mm Under the control of a mechanical device, the second permanent magnet 21 can translate along the X, Y, and Z axes directions, and can also rotate around the X and Z axes to achieve the purpose of 5-DOF control. The electromagnetic induction coil 23 is coaxially arranged with the second permanent magnet 21, and can be arranged under the second permanent magnet 21 or around the second permanent magnet 21. For example, the electromagnetic induction coil 23 consists of 500~5000 turns of copper wire with a diameter of 0.5 mm, is arranged under the second permanent magnet 21, and can follow the second permanent magnet 21 to translate along the X, Y, and Z axes directions.

In this specific embodiment, the second permanent magnet 21 provides a basic magnetic field for driving the translation, flipping and field of view adjustment, etc. of the capsule endoscope 100. The electromagnetic induction coil 23 is applied with a variable current to generate an auxiliary magnetic field with adjustable strength for fine adjustment based on the basic magnetic field, so that the orientation of the capsule endoscope 100 at a certain position can be adjusted quickly in a small range. In particular, in this system, the second permanent magnet 21 and the electromagnetic induction coil 23 cooperate with each other to control the suspension of the capsule endoscope 100 in a target area. During suspension control, the second permanent magnet 21 provides a main pulling force to make the capsule system near the equilibrium point, and the magnetic field generated by the electromagnetic induction coil 23 is mainly used to maintain the stability of the suspension. When the suspension of the capsule is stable, only a small current needs to be provided to achieve low power consumption and low heat generation.

In addition, in an embodiment of the present invention, a workstation can be optionally provided for recording, processing, and controlling the external magnetic field generating device 200 and the capsule endoscope 100. The workstation can be a server, a personal computer or a display device. The workstation is installed with corresponding operating software that can be used to display images taken by the capsule endoscope 100 and various sensor information, perform complex calculations, and control the operating status of the capsule endoscope 100 and the external magnetic field generating device 200.

Figure 3:
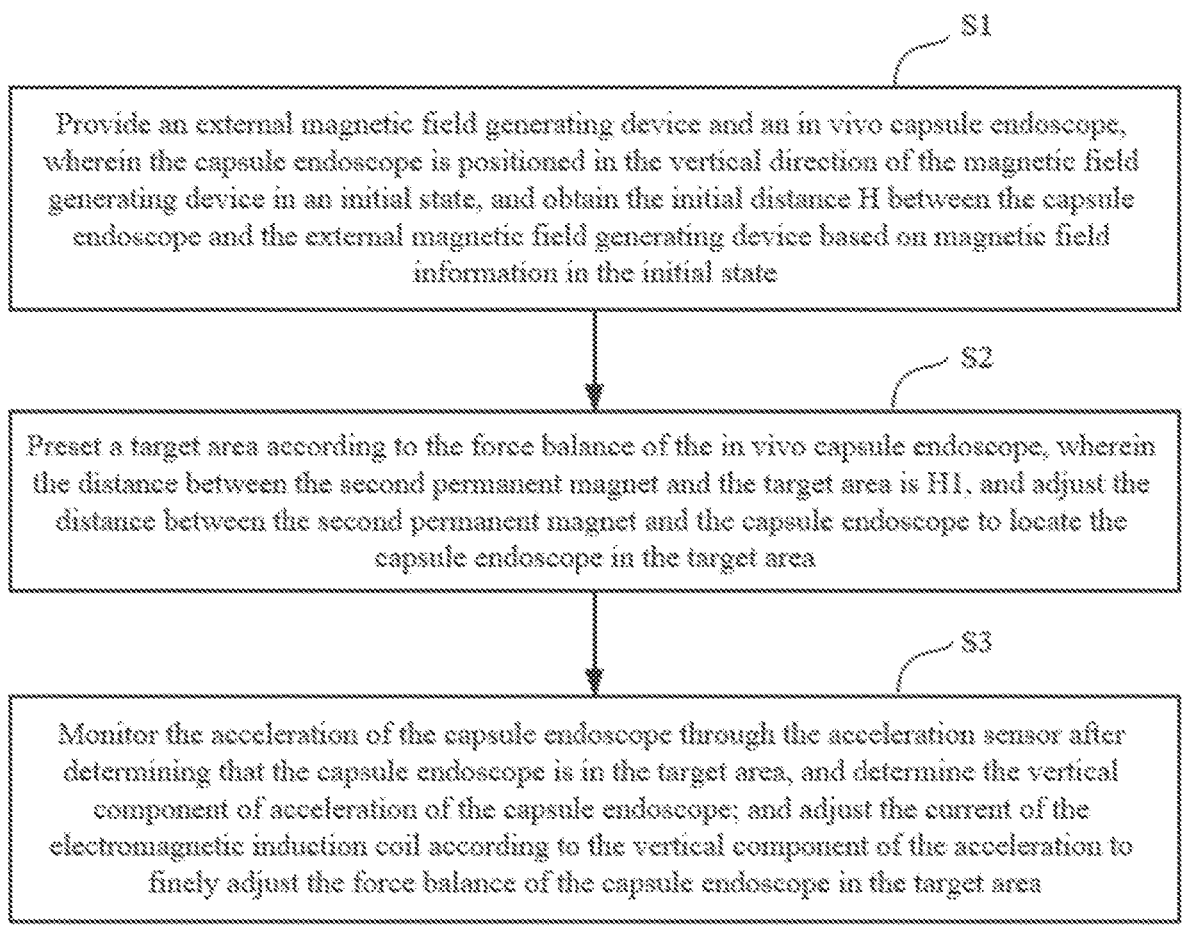
FIG. 3 is a flowchart of a control method for a capsule endoscope provided in an embodiment of the present invention.

Referring to FIG. 3, the first embodiment of the present invention provides a control method for a capsule endoscope, the method comprising:

Step S1, providing an external magnetic field generating device and an in vivo capsule endoscope, ensuring that the capsule endoscope is positioned in the vertical direction of the magnetic field generating device in an initial state to make sure that the capsule endoscope is stressed only in the vertical direction, and obtaining an initial distance H between the capsule endoscope and the external magnetic field generating device based on magnetic field information in the initial state. Wherein, the capsule endoscope comprises a first permanent magnet, a magnetic sensor, and an acceleration sensor. The external magnetic field generating device comprises a second permanent magnet configured to generate a strong basic magnetic field, and an electromagnetic induction coil configured to generate a strength-adjustable auxiliary magnetic field by applying a variable current.

Step S2, according to the force balance of the in vivo capsule endoscope, presetting a target area, the distance between the second permanent magnet and the target area is H1, and adjusting the distance between the second permanent magnet and the capsule endoscope to locate the capsule endoscope in the target area.

Step S3, after determining that the capsule endoscope is in the target area, monitoring the acceleration of the capsule endoscope through the acceleration sensor, and determining the vertical component of acceleration of the capsule endoscope; and adjusting the current of the electromagnetic induction coil according to the vertical component of the acceleration to finely adjust the force balance of the capsule endoscope in the target area.

For step S1, through the magnetic drive of the external magnetic field generating device, the capsule endoscope moves freely in the digestive tract and is controlled to pass through a certain area, such as the pylorus. Correspondingly, the step S1 specifically comprises: step S11, obtaining the magnetic field strength $\vec{B}_{mag}$ detected by the magnetic sensor 14 in the initial state, and calculating the magnetic field strength $\vec{B}_E$ generated by the second permanent magnet at the capsule endoscope 100 according to the magnetic field strength $\vec{B}_{mag}$; then, $\vec{B}_E = \vec{B}_{mag} - \vec{B}_{in} - \vec{B}_{bg}$, wherein, $\vec{B}_{in}$ is the magnetic field strength of the first permanent magnet 13 at the magnetic sensor 14, $\vec{B}_{bg}$ is an environmental background magnetic field strength; step S12, calculating the distance difference H between the capsule endoscope and the second permanent magnet according to the calculated $\vec{B}_E$.

In an exemplary embodiment of the present invention, $\vec{B}_{mag}$ is obtained by the magnetic sensor 14 through real-time monitoring. Since the relative position between the first permanent magnet 13 and the magnetic sensor 14 is fixed, $\vec{B}_{in}$ is a constant, typically 10 mT; $\vec{B}_{bg}$ is the environmental background magnetic field strength, the magnitude of which is related to the operating environment, such as geomagnetism, magnetic fields generated by other equipment in space, etc., typically in the range of 0.01~0.1 mT. That is, $\vec{B}_{in}$ and $\vec{B}_{bg}$ in the above formula are usually fixed values, so $\vec{B}_E$ can be obtained by the above formula, and further the distance difference H between the capsule endoscope and the second permanent magnet can be calculated by $\vec{B}_E$. It should be noted that the error of the distance difference H obtained in this way is on the order of millimeters, so as to achieve the purpose of coarse adjustment. Obtaining the distance between the capsule endoscope and the external magnetic field generating device by $\vec{B}_E$ is a method in the prior art, and cannot be further described here.

According to the force balance of the in vivo capsule endoscope, a target area is preset. For example, the target area is the digestive tract. It should be noted that when the technique is applied, the subject is usually required to drink more water to fill the digestive tract, so that the capsule endoscope is usually immersed in water. Accordingly, for capsule endoscope, the following formula is established:

$\vec{G}+(\vec{F}_{pm}+\vec{F}_{coil})+\vec{F}b+\vec{F}t=0$, wherein, $\vec{G}$ is the gravity of the capsule endoscope, that is typically 0.02~0.05 N, $\vec{F}_{pm}$ is the pulling force of the second permanent magnet on the capsule endoscope, $\vec{F}_{coil}$ is the magnetic force of the magnetic field of the electromagnetic induction coil on the capsule endoscope, $\vec{F}b$ is the buoyant force of the capsule endoscope when it is completely immersed in the liquid, that is typically 0.02~0.03N, and $\vec{F}t$ is the support force of the inner wall of the target area on the capsule endoscope.

Specifically, the external magnetic field generating device is usually located directly above the capsule endoscope. Based on the position relationship and the above formula, the positive and negative relationship of each parameter in the above formula can be clarified, and cannot be further described here.

In an exemplary embodiment of the present invention, in the initial state, the electromagnetic induction coil is not activated. Thus, $\vec{F}_{coil}=0$, the external magnetic field generating device is far away from the capsule endoscope, and the gravity $\vec{G}$ of the capsule endoscope is greater than the buoyant force $\vec{F}b$ when it is in water, that is, the capsule endoscope is at the bottom of the digestive tract. In order to keep the capsule endoscope in suspension, the support force of the inner wall of the digestive tract on the capsule endoscope should be satisfied: $\vec{F}t=0$, and at the same time, a pulling force should be exerted on the capsule endoscope, to satisfy the following formula: $\vec{G}+\vec{F}_{pm}+\vec{F}b\approx 0$.

In an exemplary embodiment of the present invention, the step S2 specifically comprises: step S21, in the preset target area, the force of the capsule is as follows: $\vec{G}+\vec{F}_{pm}+\vec{F}_{b}\approx 0$, where, $\vec{G}$ is the gravity of the capsule endoscope, $\vec{F}_{pm}$ is the pulling force of the second permanent magnet on the capsule endoscope, $\vec{F}_{b}$ is the buoyant force of the capsule endoscope completely immersed in the liquid, $\vec{G}$ and $\vec{F}_{b}$ are all given values, and the distance H1 between the second permanent magnet and the preset target area can be calculated according to $\vec{F}_{pm}$; step S22, moving the second permanent magnet in the vertical direction, by a distance of H−H1, to locate the capsule endoscope in the target area. Accordingly, obtaining the distance between the capsule endoscope and the external magnetic field generating device by $\vec{F}_{pm}$ is a method in the prior art, and cannot be further described here.

In an exemplary embodiment of the present invention, the step S3 specifically comprises: monitoring whether the absolute value of the vertical component of acceleration of the capsule endoscope is less than a certain threshold. If the absolute value is less than the certain threshold, controlling the electromagnetic induction coil to turn off If the absolute value is not less than the certain threshold, controlling the electromagnetic induction coil to turn on, adjusting the input current I of the electromagnetic induction coil to adjust the strength of the auxiliary magnetic field, and thereby adjusting the pushing force or pulling force on the capsule endoscope, so that the absolute value of the vertical component of acceleration of the capsule endoscope is less than the certain threshold. Wherein, I=U(t)/R, $$U(t) = K_p\left[e(t) + \frac{1}{T_i}\int e(t)dt + T_d\frac{de(t)}{dt}\right],$$

$e(t)=0-a_z(t)$, t denotes time, U(t) is the voltage across the electromagnetic induction coil at time t, R is the resistance of the electromagnetic induction coil, $K_p$ is the proportionality coefficient, $T_i$ is the integral time constant, $T_d$ is the derivative time constant, $a_z(t)$ is the vertical component of acceleration of the capsule endoscope at time t, $\int e(t)dt$ denotes integral operation, $$\frac{de(t)}{dt}$$

denotes derivative operation.

When the capsule endoscope is in the target area, in order to keep the capsule endoscope always suspended in the vertical direction, when the vertical component of the acceleration is in a upward direction, it means that the resultant force on the capsule endoscope is in an upward direction, and at this point, the current of the electromagnetic induction coil is adjusted to reduce the upward pulling force or increase the downward pressure on the capsule endoscope. When the vertical component of the acceleration is in a downward direction, it means that the resultant force on the capsule endoscope is in a downward direction, and at this point, the current of the electromagnetic induction coil is adjusted to increase the upward pulling force or reduce the downward pressure on the capsule endoscope. Accordingly, in this specific embodiment of the present invention, the vertical component of acceleration of the capsule endoscope is detected by the acceleration sensor, and then the force direction of the capsule endoscope is determined, so that the current of the electromagnetic induction coil is adjusted to indirectly make the capsule endoscope in a suspended state.

It should be noted that the magnitude of the vertical component of acceleration of the capsule endoscope cannot be completely zero. In this embodiment, the absolute value of the vertical component of acceleration being continuously less than the certain threshold, which can represent that the capsule endoscope reaches a balanced state. In addition, to achieve a better control effect, the acceleration sensor needs high-speed feedback, typically using a frequency set to 1~5 kHz, to quickly transmit data to adjust the real-time motion state of the capsule endoscope.

Figure 4:
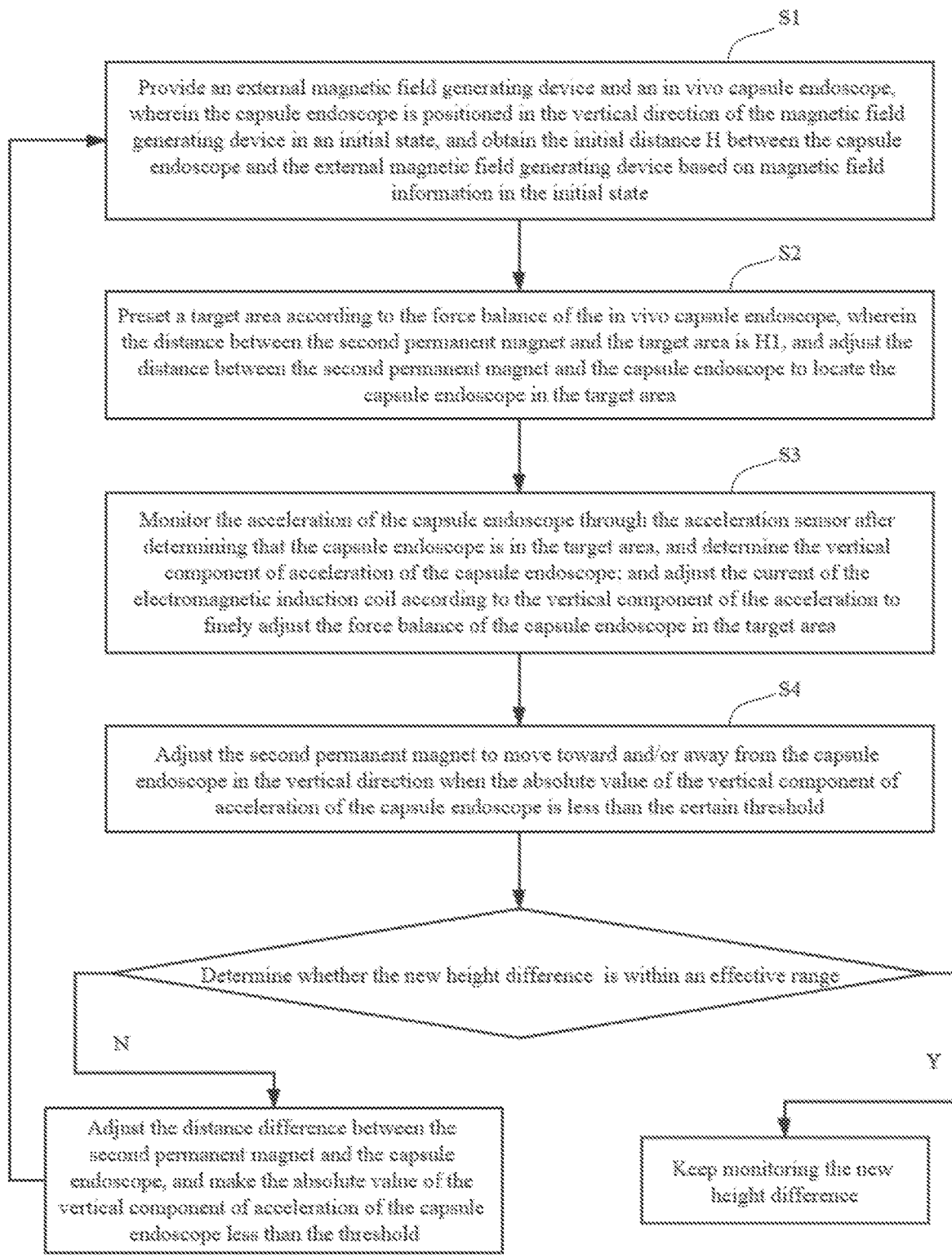
FIG. 4 is a flowchart of a control method for a capsule endoscope provided in a preferred embodiment of the present invention.

In the specific application process of the present invention, the capsule endoscope may touch the inner wall of the digestive tract and cause the acceleration detected by the acceleration sensor in the vertical direction to be 0. In this state, the capsule endoscope is not suspended. In order to overcome the problem, the method in a preferred embodiment of the present invention further comprises: using a lower monitoring frequency for monitoring and adjustment. For example, the frequency is 1 Hz or lower. Accordingly, referring to FIG. 4, the method further comprises: step S4, adjusting the second permanent magnet to move toward and/or away from the capsule endoscope in the vertical direction when the absolute value of the vertical component of acceleration of the capsule endoscope is less than the certain threshold; and determining whether the new height difference H2 between the capsule endoscope and the second permanent magnet is within an effective range. If the new height difference H2 is within the effective range, keeping monitoring. If the new height difference H2 is not within the effective range, adjusting the distance difference between the second permanent magnet and the capsule endoscope, and performing the step S1 cyclically.

The effective range is determined according to H1, and its value is equal to H1±ΔH, that is, the effective range is the specific value of H1 with an increase of the deviation range, for example: the effective range interval is (H1−ΔH, H1+ΔH), where ΔH is 2 mm for example.

In this embodiment, if a significant difference is found between H2 and H1, it means that the capsule endoscope is not moving with the external magnetic field generating device. At this time, the capsule endoscope is not suspended and may be in contact with the inner wall of the digestive tract. In order to solve this problem, when it is determined that this situation exists, adjust the distance difference between the second permanent magnet and the capsule endoscope, and perform step S1 cyclically. In the implementable embodiments of the present invention, when the external magnetic field generating device is lifted upwards, if the height difference between the capsule endoscope and the second permanent magnet increases constantly, the capsule endoscope falls on the bottom of the digestive tract. When the external magnetic field generating device is driven to move downward, if the height difference between the capsule endoscope and the second permanent magnet decreases constantly, the capsule endoscope is in contact with the top wall of the digestive tract.

An embodiment of the present invention provides an electronic device, comprising a memory and a processor. The memory stores a computer program that can run on the processor, and the processor executes the program to implement the steps of the control method for the capsule endoscope described above.

An embodiment of the present invention provides a computer-readable storage medium for storing computer programs. The computer programs are executed by the processor to implement the steps of the control method for the capsule endoscope described above.

Figure 5:
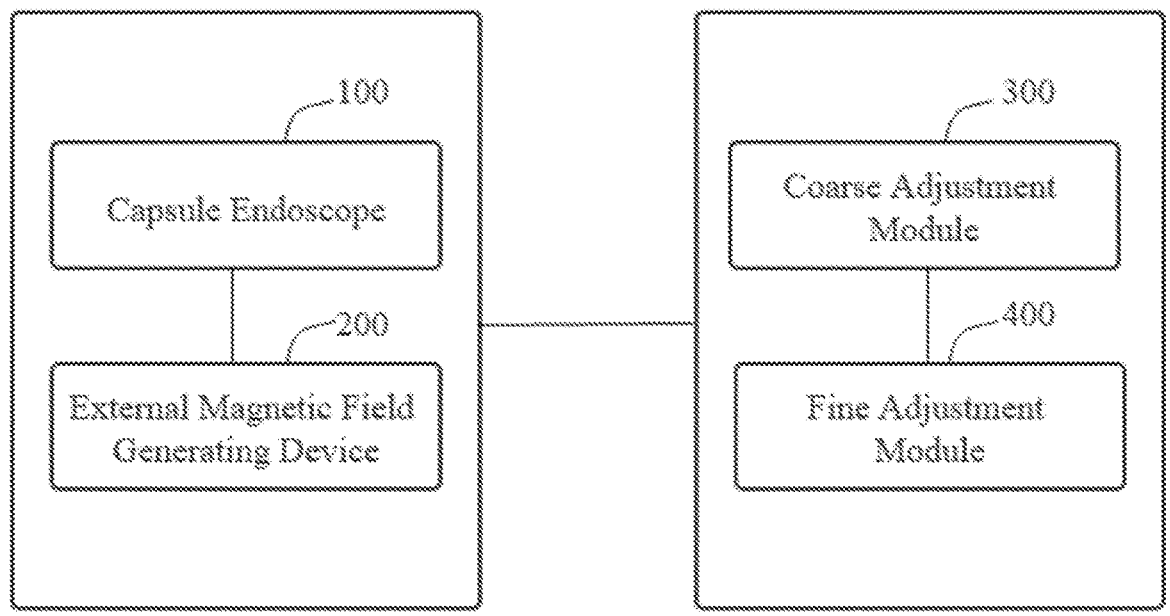
FIG. 5 is a schematic diagram of modules of a control system for a capsule endoscope in an embodiment of the present invention.

Referring to FIG. 5, an embodiment of the present invention provides a control system for a capsule endoscope, comprising the capsule endoscope 100 and the external magnetic field generating device 200. The system further comprising: a coarse adjustment module 300 and a fine adjustment module 400.

The coarse adjustment module 300 is used for presetting a target area according to the force balance of the in vivo capsule endoscope, and the distance between the second permanent magnet and the target area is H1; and obtaining an initial distance H between the capsule endoscope and the external magnetic field generating device in the initial state according to the magnetic field information, and adjusting the distance between the second permanent magnet and the capsule endoscope according to the magnitude relationship between H and H1, so as to locate the capsule endoscope in the target area. The fine adjustment module 400 is used for monitoring the acceleration of the capsule endoscope through an acceleration sensor after determining that the capsule endoscope is in the target area, and determining the vertical component of acceleration of the capsule endoscope; and adjusting the current of the electromagnetic induction coil according to the vertical component to finely adjust the force balance of the capsule endoscope in the target area.

In a preferred embodiment of the present invention, the coarse adjustment module 300 is specifically used for: obtaining the magnetic field strength $\vec{B}_{mag}$ detected by the magnetic sensor in the initial state, and calculating the magnetic field strength $\vec{B}_E$ generated by the second permanent magnet at the capsule endoscope according to $\vec{B}_{mag}$; then, $\vec{B}_E = \vec{B}_{mag} - \vec{B}_{in} - \vec{B}_{bg}$, wherein, $\vec{B}_{in}$ is the magnetic field strength of the first permanent magnet at the magnetic sensor, $\vec{B}_{bg}$ is the environmental background magnetic field strength; and calculating the distance difference H between the capsule endoscope and the second permanent magnet according to the calculated $\vec{B}_E$.

Further, the coarse adjustment module 300 is specifically used for: in the preset target area, the force of the capsule is as follows: $\vec{G} + \vec{F}_{pm} + \vec{F}_b \approx 0$, wherein, $\vec{G}$ is the gravity of the capsule endoscope, $\vec{F}_{pm}$ is the pulling force of the second permanent magnet on the capsule endoscope, $\vec{F}_b$ is the buoyant force of the capsule endoscope completely immersed in the liquid, $\vec{G}$ and $\vec{F}_b$ are all given values, and the distance H1 between the second permanent magnet and the preset target area can be calculated according to $\vec{F}_{pm}$; and moving the second permanent magnet in the vertical direction, by a distance of H−H1, to locate the capsule endoscope in the target area.

The fine adjustment module 400 is specifically used for: monitoring whether the absolute value of the vertical component of acceleration of the capsule endoscope is less than a certain threshold. If the absolute value is less than the certain threshold, controlling the electromagnetic induction coil to turn off. If the absolute value is not less than the certain threshold, controlling the electromagnetic induction coil to turn on, adjusting the input current I of the electromagnetic induction coil to adjust the strength of the auxiliary magnetic field, and thereby adjusting the pushing or pulling force on the capsule endoscope, so that the absolute value of the vertical component of acceleration of the capsule endoscope is less than the certain threshold. Wherein, I=U(t)/R, $$U(t) = K_p \left[ e(t) + \frac{1}{T_i} \int e(t)dt + T_d \frac{de(t)}{dt} \right],$$

e(t)=0−a_z(t), t denotes time, U(t) is the voltage across the electromagnetic induction coil at time t, R is the resistance of the electromagnetic induction coil, $K_p$ is the proportionality coefficient, $T_i$ is the integral time constant, $T_d$ is the derivative time constant, $a_z(t)$ is the vertical component of acceleration of the capsule endoscope at time t, ∫e(t)dt denotes integral operation, $$\frac{de(t)}{dt}$$

denotes derivative operation.

Figure 6:
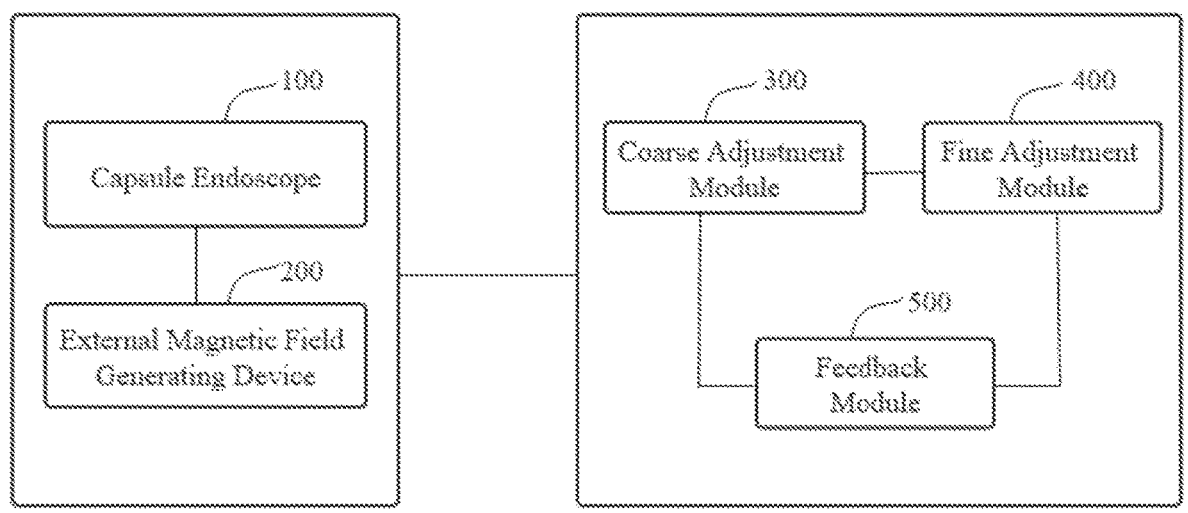
FIG. 6 is a schematic diagram of modules of a control system for a capsule endoscope in a preferred embodiment of the present invention.

Referring to FIG. 6, in a preferred embodiment of the present invention, a control system for the capsule endoscope is provided. This embodiment is improved on the embodiment shown in FIG. 6, and the difference is that the control system further comprises a feedback module 500. The feedback module 500 is used for adjusting the second permanent magnet to move toward and/or away from the capsule endoscope in the vertical direction when the absolute value of the vertical component of acceleration of the capsule endoscope is less than the certain threshold; and determining whether the new height difference between the capsule endoscope and the second permanent magnet is within an effective range. If the new height difference H2 is within the effective range, keeping monitoring. If the new height difference H2 is not within the effective range, adjusting the distance difference between the second permanent magnet and the capsule endoscope, and making the absolute value of the vertical component of acceleration of the capsule endoscope less than the certain threshold through the cooperation of the coarse adjustment module and the fine adjustment module.

Those skilled in the art can clearly understand that, for the convenience and conciseness of the description, the specific working process of the system described above cannot be repeated as it has been detailed in the foregoing method implementation.

It can be seen from the above that the present invention mainly relies on the high-speed feedback of the acceleration sensor to maintain the suspending state of the capsule endoscope. The magnetic sensor only needs to be turned on occasionally during the coarse adjustment stage and the monitoring stage, and the frequency of use is low, so it can greatly save the use of high-power chips. In addition, the acceleration sensor is free from magnetic field interference when measuring the acceleration of the capsule endoscope, and the magnetic field interference can be caused by the internal magnet difference of the capsule endoscope, environmental magnetic field fluctuations, and/or electromagnetic coil current fluctuations, etc. Moreover, the acceleration sensor comes with low power consumption and high sampling rate, and can meet the requirements for closed-loop magnetic control of suspension.

In summary, the control method, control system, electronic device and readable storage medium for capsule endoscope of the present invention, coarsely adjust the position of the capsule endoscope based on the detection results of a magnetic sensor, and perform position monitoring, and then finely adjust the position of the capsule endoscope based on the feedback signal of an acceleration sensor and the assistance of an external electromagnetic induction coil, so as to enable the capsule endoscope to reach a suspended state.

For the convenience of description, the device is described in various modules divided by functions separately. When implementing the present invention, the functions of the various modules can be implemented in the same or different software and/or hardware.

The device implementations described above are merely illustrative. The modules described as separate components may or may not be physically separated, and the components displayed as modules may or may not be physical modules, that is, they may be located in one place, or may also be distributed over a plurality of network modules. Some or all of the modules may be selected according to actual needs to achieve the object of the embodiment. It can be understood and implemented by ordinary persons skilled in the art without creative work.

It should be understood that, although the specification is described in terms of embodiments, not every embodiment merely includes an independent technical solution. This narration in the specification is only for clarity. Those skilled in the art should have the specification as a whole, and the technical solutions in each embodiment may also be combined as appropriate to form other embodiments that can be understood by those skilled in the art.

The series of detailed descriptions listed above are only specific descriptions of the feasible embodiments of the present invention, and are not intended to limit the protection scope of the present invention. Any equivalent embodiments or variations made without departing from the technical spirit of the present invention should be included in the protection scope of the present invention.

What is claimed is:

1. A control method for a capsule endoscope, comprising:
providing an external magnetic field generating device and an in vivo capsule endoscope, wherein the capsule endoscope is positioned in the vertical direction of the magnetic field generating device in an initial state, and
obtaining the initial distance H between the capsule endoscope and the external magnetic field generating device based on magnetic field information in the initial state;
wherein, the capsule endoscope comprises
a first permanent magnet,
a magnetic sensor and an acceleration sensor, and
the external magnetic field generating device comprises
a second permanent magnet for generating a strong basic magnetic field and an electromagnetic induction coil for generating a strength-adjustable auxiliary magnetic field by applying a variable current;
presetting a target area according to the force balance of the in vivo capsule endoscope, wherein the distance between the second permanent magnet and the target area is H1, and adjusting the distance between the second permanent magnet and the capsule endoscope to locate the capsule endoscope in the target area;
monitoring the acceleration of the capsule endoscope through the acceleration sensor after determining that the capsule endoscope is in the target area, and
determining the vertical component of acceleration of the capsule endoscope; and adjusting the current of the electromagnetic induction coil according to the vertical component of the acceleration to finely adjust the force balance of the capsule endoscope in the target area,
wherein the distance H between the capsule endoscope and the second permanent magnet is obtained by:
obtaining magnetic field strength $\vec{B}_{mag}$ detected by the magnetic sensor in the initial state, and calculating magnetic field strength $\vec{B}_E$ generated by the second permanent magnet at the capsule endoscope according to the magnetic field strength $\vec{B}_{mag}$;
$\vec{B}_E = \vec{B}_{mag} - \vec{B}_{in} - \vec{B}_{bg}$ is magnetic field strength of the first permanent magnet at the magnetic sensor, and $\vec{B}_{bg}$ is the environmental background magnetic field strength;
calculating the distance difference H between the capsule endoscope and the second permanent magnet according to the calculated $\vec{B}_E$.

2. The control method of claim 1, wherein locating the capsule endoscope in the target area by:
calculating the distance H1 between the second permanent magnet and the target area according to the pulling force $\vec{F}_{pm}$ of the second permanent magnet on the capsule endoscope, wherein the force of the capsule endoscope in the target area is as follows: $\vec{G} + \vec{F}_{pm} + \vec{F}_b \approx 0$, wherein $\vec{G}$ is the gravity of the capsule endoscope, $\vec{F}_{pm}$ is the pulling force of the second permanent magnet on the capsule endoscope, $\vec{F}_b$ is the buoyant force of the capsule endoscope completely immersed in the liquid, $\vec{G}$ and $\vec{F}_b$ are given values;

moving the second permanent magnet in the vertical direction, by a distance of H-H1, to locate the capsule endoscope in the target area.

3. The control method of claim 1, wherein adjusting the current of the electromagnetic induction coil by:

monitoring whether the absolute value of the vertical component of acceleration of the capsule endoscope is less than a certain threshold;

controlling the electromagnetic induction coil to turn off when the absolute value is less than the certain threshold;

controlling the electromagnetic induction coil to turn on when the absolute value is not less than the certain threshold, adjusting the input current I of the electromagnetic induction coil to adjust the strength of the auxiliary magnetic field, and thereby adjusting the pushing force or pulling force on the capsule endoscope, so that the absolute value of the vertical component of acceleration of the capsule endoscope is less than the certain threshold;

wherein, I=U(t)/R, $$U(t) = K_p \left[ e(t) + \frac{1}{T_i} \int e(t)dt + T_d \frac{de(t)}{dt} \right],$$

e(t)=0−$a_z$(t), t denotes time, U(t) is the voltage across the electromagnetic induction coil, R is the resistance of the electromagnetic induction coil, $K_p$ is the proportionality coefficient, $T_i$ is the integral time constant, $T_d$ is the derivative time constant, $a_z$(t) is the vertical component of acceleration of the capsule endoscope at time t, ∫e(t)dt is integral operation, $$\frac{de(t)}{dt}$$

is derivative operation.

4. The control method of claim 1, wherein the method further comprises:

adjusting the second permanent magnet to move toward and/or away from the capsule endoscope in the vertical direction when the absolute value of the vertical component of acceleration of the capsule endoscope is less than the certain threshold, and determining whether the new height difference between the capsule endoscope and the second permanent magnet is within an effective range;

monitoring the new height difference when the new height difference is within the effective range, where the capsule can be moved by the magnet or within the working field;

adjusting the distance difference between the second permanent magnet and the capsule endoscope, and making the absolute value of the vertical component of acceleration of the capsule endoscope less than the threshold when the new height difference is not within the effective range.

5. An electronic device, comprising a memory and a processor, the memory stores computer programs, and the processor executes the computer programs to implement the steps of a control method for a capsule endoscope, wherein the method comprises:

providing an external magnetic field generating device and an in vivo capsule endoscope, wherein the capsule endoscope is positioned in the vertical direction of the magnetic field generating device in an initial state, and obtaining the initial distance H between the capsule endoscope and the external magnetic field generating device based on magnetic field information in the initial state; wherein, the capsule endoscope comprises a first permanent magnet, a magnetic sensor and an acceleration sensor, and the external magnetic field generating device comprises a second permanent magnet for generating a strong basic magnetic field and an electromagnetic induction coil for generating a strength-adjustable auxiliary magnetic field by applying a variable current;

presetting a target area according to the force balance of the in vivo capsule endoscope, wherein the distance between the second permanent magnet and the target area is H1, and adjusting the distance between the second permanent magnet and the capsule endoscope to locate the capsule endoscope in the target area;

monitoring the acceleration of the capsule endoscope through the acceleration sensor after determining that the capsule endoscope is in the target area, and determining the vertical component of acceleration of the capsule endoscope; and adjusting the current of the electromagnetic induction coil according to the vertical component of the acceleration to finely adjust the force balance of the capsule endoscope in the target area, wherein the distance H between the capsule endoscope and the second permanent magnet is obtained by:

obtaining magnetic field strength $\vec{B}_{mag}$ detected by the magnetic sensor in the initial state, and calculating magnetic field strength $\vec{B}_B$ generated by the second permanent magnet at the capsule endoscope according to the magnetic field strength $\vec{B}_{mag}$;

$\vec{B}_E = \vec{B}_{mag} - \vec{B}_{in} - \vec{B}_{bg}$ is magnetic field strength of the first permanent magnet at the magnetic sensor, and $\vec{B}_{bg}$ is the environmental background magnetic field strength;

calculating the distance difference H between the capsule endoscope and the second permanent magnet according to the calculated $\vec{B}_E$.

6. A computer-readable storage medium, storing computer programs, wherein the computer programs can be executed by the processor to implement the steps of a control method for a capsule endoscope, wherein the method comprises:

providing an external magnetic field generating device and an in vivo capsule endoscope, wherein the capsule endoscope is positioned in the vertical direction of the magnetic field generating device in an initial state, and obtaining the initial distance H between the capsule endoscope and the external magnetic field generating device based on magnetic field information in the initial state; wherein, the capsule endoscope comprises a first permanent magnet, a magnetic sensor and an acceleration sensor, and the external magnetic field generating device comprises a second permanent magnet for generating a strong basic magnetic field and an electromagnetic induction coil for generating a strength-adjustable auxiliary magnetic field by applying a variable current;

presetting a target area according to the force balance of the in vivo capsule endoscope, wherein the distance between the second permanent magnet and the target area is H1, and adjusting the distance between the second permanent magnet and the capsule endoscope to locate the capsule endoscope in the target area;

monitoring the acceleration of the capsule endoscope through the acceleration sensor after determining that the capsule endoscope is in the target area, and determining the vertical component of acceleration of the capsule endoscope; and adjusting the current of the electromagnetic induction coil according to the vertical component of the acceleration to finely adjust the force balance of the capsule endoscope in the target area, wherein the distance H between the capsule endoscope and the second permanent magnet is obtained by:

obtaining magnetic field strength $\vec{B}_{mag}$ detected by the magnetic sensor in the initial state, and calculating magnetic field strength $\vec{B}_E$ generated by the second permanent magnet at the capsule endoscope according to the magnetic field strength $\vec{B}_{mag}$;

$\vec{B}_E = \vec{B}_{mag} - \vec{B}_{in} - \vec{B}_{bg}$, wherein, $\vec{B}$ in is magnetic field strength of the first permanent magnet at the magnetic sensor, and $\vec{B}_{bg}$ is the environmental background magnetic field strength;

calculating the distance difference H between the capsule endoscope and the second permanent magnet according to the calculated $\vec{B}_E$.

7. A control system for a capsule endoscope, comprising:
a capsule endoscope, comprising a first permanent magnet, a magnetic sensor and an acceleration sensor;
an external magnetic field generating device, which is positioned in the vertical direction of the capsule endoscope in an initial state, comprising: a second permanent magnet for generating a strong basic magnetic field, and an electromagnetic induction coil for generating a strength-adjustable auxiliary magnetic field by applying a variable current;
a coarse adjustment module, for presetting a target area according to the force balance of the in vivo capsule endoscope, wherein the distance between the second permanent magnet and the target area is H1;
the coarse adjustment module for obtaining an initial distance H between the capsule endoscope and the external magnetic field generating device in the initial state according to the magnetic field information, and adjusting the distance between the second permanent magnet and the capsule endoscope according to the magnitude relationship between H and H1, so as to locate the capsule endoscope in the target area;
a fine adjustment module, for monitoring the acceleration of the capsule endoscope through the acceleration sensor after determining that the capsule endoscope is in the target area, determining the vertical component of acceleration of the capsule endoscope, and adjusting the current of the electromagnetic induction coil according to the vertical component of the acceleration to finely adjust the force balance of the capsule endoscope in the target area, wherein the coarse adjustment module for:
obtaining magnetic field strength $\vec{B}_{mag}$ detected by the magnetic sensor in the initial state, and calculating magnetic field strength $\vec{B}_E$ generated by the second permanent magnet at the capsule endoscope according to the magnetic field strength $\vec{B}_{mag}$;

$\vec{B}_E = \vec{B}_{mag} - \vec{B}_{in} - \vec{B}_{bg}$, wherein, $\vec{B}$ in is magnetic field strength of the first permanent magnet at the magnetic sensor, and $\vec{B}_{bg}$ is the environmental background magnetic field strength; and calculating the distance difference H between the capsule endoscope and the second permanent magnet according to the calculated $\vec{B}_E$.

8. The control system of claim 7, wherein the coarse adjustment module for:
calculating the distance H1 between the second permanent magnet and the target area according to the pulling force $\vec{F}_{pm}$ of the second permanent magnet on the capsule endoscope, wherein the force of the capsule endoscope in the target area is as follows: $\vec{G} + \vec{F}_{pm} + \vec{F}_b \approx 0$, wherein, $\vec{G}$ is the gravity of the capsule endoscope, $\vec{F}_{pm}$ is the pulling force of the second permanent magnet on the capsule endoscope, $\vec{F}_b$ is the buoyant force of the capsule endoscope completely immersed in the liquid, $\vec{G}$ and $\vec{F}_b$ are all given values; and moving the second permanent magnet in the vertical direction, by a distance of H-H1, to locate the capsule endoscope in the target area.

9. The control system of claim 7, wherein the fine adjustment module for:
monitoring whether the absolute value of the vertical component of acceleration of the capsule endoscope is less than a certain threshold;
controlling the electromagnetic induction coil to turn off when the absolute value is less than the certain threshold;
controlling the electromagnetic induction coil to turn on when the absolute value is not less than the certain threshold, adjusting the input current I of the electromagnetic induction coil to adjust the strength of the auxiliary magnetic field, and thereby adjusting the pushing force or pulling force on the capsule endoscope, so that the absolute value of the vertical component of acceleration of the capsule endoscope is less than the certain threshold;
wherein, I=U(t)/R, $$U(t) = K_p \left[ e(t) + \frac{1}{T_i} \int e(t)dt + T_d \frac{de(t)}{dt} \right],$$

e(t)=0−$a_z$(t), denotes time, U(t) is the voltage across the electromagnetic induction coil, R is the resistance of the electromagnetic induction coil, $K_p$ is the proportionality coefficient, $T_i$ is the integral time constant, $T_d$ is the derivative time constant, $a_z$(t) is the vertical component of acceleration of the capsule endoscope at time t, $\int e(t)dt$ is integral operation, $$\frac{de(t)}{dt}$$

is derivative operation.

10. The control system of claim 7, wherein the system further comprises:
a feedback module, for adjusting the second permanent magnet to move toward and/or away from the capsule endoscope in the vertical direction when the absolute value of the vertical component of acceleration of the capsule endoscope is less than the certain threshold, and determining whether the new height difference between the capsule endoscope and the second permanent magnet is within an effective range, where the capsule can be moved by the magnet or within the working field;

monitoring the new height difference when the new height difference is within the effective range;

adjusting the distance difference between the second permanent magnet and the capsule endoscope, and making the absolute value of the vertical component of acceleration of the capsule endoscope less than the threshold when the new height difference is not within the effective range.

\* \* \* \* \*